(12) United States Patent
Muller et al.

(10) Patent No.: US 6,818,000 B2
(45) Date of Patent: *Nov. 16, 2004

(54) ELECTRODE ARRANGEMENT FOR ELECTROTHERMAL TREATMENT OF HUMAN OR ANIMAL BODIES

(75) Inventors: Gerhard Muller, Berlin (DE); Kai Desinger, Berlin (DE); Thomas Stein, Kurfurstenstrasse (DE)

(73) Assignee: Celon AG Medical Instruments, Teltow/Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/325,518

(22) Filed: Dec. 19, 2002

(65) Prior Publication Data

US 2003/0097130 A1 May 22, 2003

Related U.S. Application Data

(63) Continuation of application No. 09/508,045, filed as application No. PCT/DE98/02695 on Sep. 4, 1998, now Pat. No. 6,524,308.

(30) Foreign Application Priority Data

Sep. 4, 1997 (DE) .......................................... 197 39 699

(51) Int. Cl.[7] .............................................. A61B 18/18
(52) U.S. Cl. .......................... 606/41; 128/898; 606/27; 606/32
(58) Field of Search ..................... 128/898; 606/27–50; 607/101–105

(56) References Cited

U.S. PATENT DOCUMENTS 4,411,266 A * 10/1983 Cosman ........................ 606/49
5,122,137 A    6/1992 Lennox
5,190,539 A *  3/1993 Fletcher et al. ................ 606/25
5,342,357 A *  8/1994 Nardella ........................ 606/40
5,545,161 A *  8/1996 Imran ........................... 606/41
5,588,960 A   12/1996 Edwards et al.
5,620,479 A    4/1997 Diederich
5,643,197 A    7/1997 Brucker et al.
5,697,927 A   12/1997 Imran et al.
5,735,846 A    4/1998 Panescu et al.
5,837,003 A * 11/1998 Ginsburg ..................... 607/106
5,906,613 A *  5/1999 Mulier et al. ................. 606/41
5,928,159 A *  7/1999 Eggers et al. ................. 606/41
6,524,308 B1 * 2/2003 Muller et al. ................. 606/49
6,575,969 B1 * 6/2003 Rittman et al. ............... 606/41

FOREIGN PATENT DOCUMENTS

| DE | 3930451 A1 | | 3/1991 | |
|---|---|---|---|---|
| WO | WO96/34571 | * | 5/1996 | ........... A61B/17/39 |
| WO | WO 96/18349 | | 6/1996 | |
| WO | WO 96/34569 | | 11/1996 | |
| WO | WO 96/34571 | | 11/1996 | |
| WO | WO 97/00647 | | 1/1997 | |
| WO | WO 97/06739 | | 2/1997 | |
| WO | WO 97/17009 | | 5/1997 | |

* cited by examiner

Primary Examiner—Roy D. Gibson
Assistant Examiner—Henry M Johnson, III
(74) Attorney, Agent, or Firm—Christie, Parker & Hale, LLP

(57) ABSTRACT

An electrode arrangement is provided having at least one electrode for insertion into a human or animal body for electrothermal treatment of the body. The electrode is situated on an electrode support and is connected to an alternating current source via a supply lead and to a temperature stabilizer device for influencing the effective temperature profile in a treatment area. The electrode support and the electrode, or electrodes, are constructed for direct insertion into body tissue, said insertion being channel forming. The temperature stabilizer device has a timed heating device.

27 Claims, 12 Drawing Sheets ically designed in such a
ELECTRODE ARRANGEMENT FOR ELECTROTHERMAL TREATMENT OF HUMAN OR ANIMAL BODIES

CROSS-REFERENCE TO RELATED APPLICATION

This application is a Continuation of U.S. patent application Ser. No. 09/508,045, filed on Mar. 3, 2000, now U.S. Pat. No. 6,529,308 which is a National Phase Patent Application of International Application No. PCT/DE98/02695, filed on Sep. 4, 1998 which claims priority of German Application No. 197 39 699.2, filed on Sep. 4, 1997 the contents all of which are incorporated herein by reference.

FIELD OF THE INVENTION

The invention relates to electrode arrangement for electrothermal treatment of the human or animal body, and in particular to electrocoagulation.

BACKGROUND OF THE INVENTION

The application of high-frequency (HF) alternating currents (specifically in the frequency range of between 300 kHz and 2 MHz) to generate high temperatures for tissue coagulation as a surgical procedure has long been known. In practice monopolar or bipolar electrode arrangements are used for introducing the HF-current into the tissue.

In the case of the monopolar arrangements, an electrode—also referred to as the neutral electrode—is designed in the form of a patient delivery line of large area and fixed to the patient not too far away from the point of intervention and earthed or connected to ground. A second electrode which is manipulated by the operator—also referred to as the active electrode—is connected to the alternating or HF current generator. In terms of its shape, the second electrode is selected to be adapted to the respective use involved, in particular the size of the tissue region to be treated, in such a way that both the operational time and also the thermal loading of the region of the body or organ involved are reasonable.

In the case of arrangements for bipolar HF-surgery, both electrodes are connected to the HF-generator and are of mutually comparable dimensions, and are placed by the operator in the immediate proximity of the intervention location and are generally also both guided actively. Bipolar electrode arrangements are also known in which both coagulation electrodes are arranged on a catheter.

WO 97/17009 discloses a bipolar electrode arrangement with a fluid duct, by way of which flushing fluid can be introduced into the operational area.

WO 96/34569 and the documents referred to in the international search report disclose systems and processes for the ablation of body tissue while maintaining a pre-calculated maximum tissue temperature, in which fluid cooling or thermoelectric cooling is provided during the actual tissue coagulation procedure. Those known arrangements are intended for the introduction into body cavities by way of natural accesses.

SUMMARY OF THE INVENTION

The object of the present invention is to provide an electrode arrangement which permits quick and easy interstitial tissue coagulation.

The present invention includes the basic teaching that the electrode arrangement is mechanically designed in such a way as to facilitate direct penetration into body tissue and at the same time thermal means are provided for setting an advantageous effective temperature profile for the insertion phase.

That notion is based on the fact that the known arrangements which are cooled during the actual electrothermy procedure have admittedly afforded many advantages, but they are not well suited to being inserted into body tissue directly (invasively), with duct formation, for interstitial use. For that reason, in clinical practice, in many cases a duct to the treatment region is firstly opened with a separate incision instrument and in an additional working step on the part of the operator, before the electrothermy applicator is advanced in the duct.

It is further based on the realization on the part of the inventors that a "cold" applicator can be inserted with more difficulty than one which has been warmed somewhat.

A short-term temperature control procedure to a temperature above about 30° C., more especially somewhat above body temperature, has proven to be advantageous for the insertion phase. As soon as the applicator has reached the treatment location and the actual electrothermal treatment is initiated, the procedure involves implementing a transition to adjusting an effective temperature profile which is optimized in regard to optimum coagulation performance. Even in periods of time of that phase, heating in addition to the generation of heat by way of the electrodes can be desirable.

In a particularly effective and at the same time inexpensive embodiment the electrode or electrodes or the electrode carrier are provided with a cavity which is closed off in relation to the body and which is connected to a fluid source which can be the subject of temperature control within a predetermined range so that the suitably temperature-controlled fluid flows through the electrode or the carrier thereof.

Distilled water is preferably used as the fluid, having regard to the low costs involved and the simple and safe handling thereof. In addition for specific situations of use—possibly having regard to specific safety precautions—it is also possible to use other fluids which have proven their worth as heat-transfer agents, as such, for example compressed air, carbon dioxide or silicone oil.

In another possible embodiment the electrode or the electrode carrier has a thermoelectric heating and cooling device which can be for example in the form of a combination of resistance heaters and Peltier elements.

In an embodiment which is simple to produce and handle, the electrode carrier is preferably a tubular, in particular cylindrical element of electrically insulating material, on the peripheral surface of which is or are arranged one or more electrodes and in the interior of which is arranged the temperature control device. To facilitate penetration into the tissue, the electrode carrier desirably has a distal end which decreases or tapers to an approximately conical tip, and the electrodes are fitted substantially flush into the peripheral surface of the carrier.

In the preferred embodiment, in the form of a bipolar arrangement, the assembly includes two electrodes which are mounted to one and the same electrode carrier, in particular in an axial row. In that case, a common temperature control device is provided for both electrodes, such as, for example, the above-mentioned internal tube counterflow temperature control device.

In the preferred embodiment of this alternative configuration, the carrier element is of a cylindrical cross-section, while the two electrodes are of a hollow-cylindrical design and are arranged coaxially with respect to the longitudinal axis of the carrier element. For that purpose the electrodes can be disposed for example in the form of a metallic coating on the surface of the carrier element or each comprise a metal sleeve (for example of titanium or Nitinol) which is pushed onto the carrier element or better inserted flush and forms therewith a press fit.

In a particularly simple embodiment of this arrangement, which is safe and secure in terms of handling, axial fixing of the electrodes is not effected by a continuous carrier element, but by a hollow connecting element which connects the electrodes (which are also hollow) together at their ends. Besides axial fixing of the electrodes, the connecting element also performs the function of insulating the two electrodes relative to each other and it therefore comprises an electrically insulating material, preferably PEEK (polyethyletherketone). The electrodes, the connecting portion and the supply line for the cooling agent (for example a relatively stiff PTFE-hoze which at the same times serves as a handle or gripping portion) are preferably annular or tubular and are of the same cross-section so that the surface of the catheter is a closed cylindrical configuration, whereby insertion into the body is facilitated and at the same time unwanted current density peaks can be substantially avoided.

In an alternative configuration of the preferred bipolar arrangement, which can be used in a particularly variable fashion, but which is more expensive in regard to structure, the axial spacing between the two electrodes is adjustable in order to be able to additionally vary the current density distribution and thus the heating output distribution. If the insulator length between the two electrodes in the axial direction is, for example, less than double the electrode diameter, it is advantageously possible to produce spherical coagulation necroses whereas the shape of the coagulation necroses with greater insulator lengths is rather oval.

The geometrical configuration of tissue coagulation can be substantially influenced by the temperature control effect—specifically by the choice of heating/cooling in a given sequence in respect of time.

In a preferred embodiment, besides the electrode or electrodes and the actual cooling device, an electrosurgery apparatus, which makes use of the invention, includes control means for establishing an advantageous effective temperature profile in the treatment region. The control means include, in particular, an effective temperature profile control device for controlling the heating or cooling output and/or the spatial distribution thereof, said control device being connected to the cooling device by way of a control signal connection for supplying a heating and/or cooling output control signal.

The effective temperature profile control device can also be adapted to produce and supply a heating output control signal for controlling the HF current power and/or the spatial distribution thereof, and can be connected to the alternating current source by way of a control input so that, besides the cooling device, it can also control the HF-source—acting as a "heating device" in the tissue. That provides for particularly flexible control of the treatment regime in the event of longer-duration intervention procedures.

The effective temperature profile control device preferably includes an interactively programmable calculation unit for determining simulated time-dependent effective temperature profiles on the basis of parameters of the tissue and the electrode arrangement and assumed parameters of the HF current source and the heating or cooling device and for effecting a variation in the assumed parameters to ascertain an optimized effective temperature profile. In practice, use will be made of a PC with which the spatial temperature distribution and optionally the time-dependency thereof can be determined and on the screen of which the simulated effective temperature profiles can be represented as an image. That already makes it considerably easier for the operator, prior to an intervention procedure, to select a suitable combination of control values of the temperature control device and the HF-source.

Placing at least one temperature sensor, which responds with a low level of inertia and which is connected to an input of the effective temperature profile control device, at a predetermined position relative to the electrode arrangement in the body, in particular at an electrode or the electrode carrier, makes it possible to implement verification or rescaling of a simulated effective temperature profile during the intervention. The parameters which are to be used in the further course of the treatment can, therefore, be freshly adjusted at any moment in time.

Additional possible options in that respect are afforded by the provision of a device for ascertaining (especially in time-dependent fashion) the heating or cooling output produced by the temperature control device or a value influencing the heating or cooling output, and a device for ascertaining the HF current power outputted by the HF current source, or a value influencing such current power.

Insofar as the effective temperature profile control device preferably has means for determining and storing a time-dependency of the cooling output control signal and/or the heating output control signal and for outputting the respective control signal in accordance with the stored time-dependency, a treatment which is established in advance in terms of the operations to be performed by the operator can take place substantially automatically, in regard to the control values. It will be appreciated in that respect that current changes in the control values still remain possible so that the operator can also react flexibly to unforeseen events. As changes of that kind can be detected and can be incorporated into an updated simulation calculation, the consequences for further progress of the intervention procedure can in turn be made clear to the doctor in a virtually real-time mode.

BRIEF DESCRIPTION OF THE DRAWINGS

Advantageous developments of the invention are moreover characterized in the appendant claims or are set forth in greater detail hereinafter together with the description of the preferred embodiment of the invention with reference to the Figures in which:

DETAILED DESCRIPTION OF THE INVENTION

Figure 1:
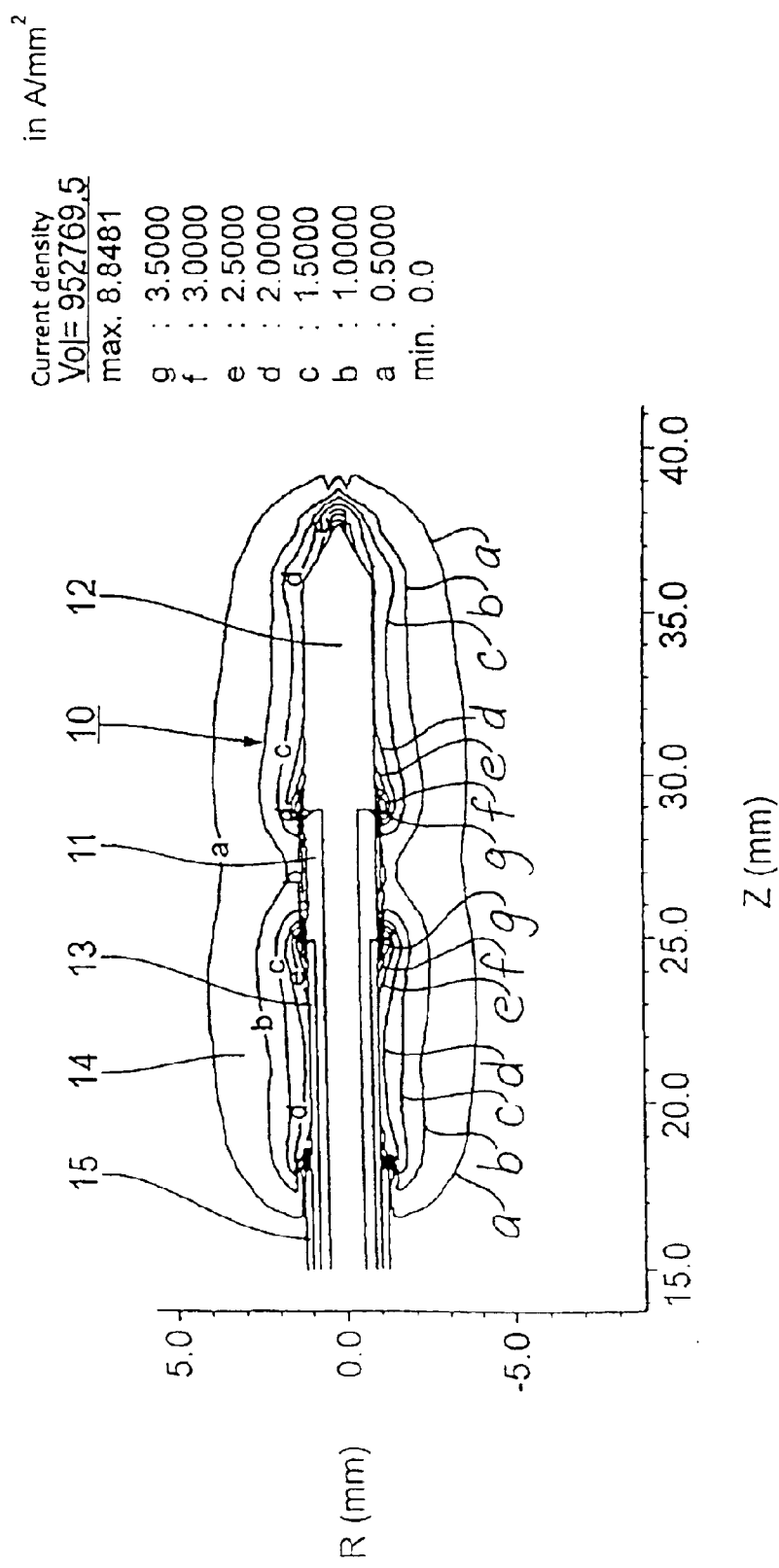
FIG. 1 is a graph view of a current density distribution, obtained as the result of a simulation calculation, along a bipolar electrode arrangement with two axially mutually displaced annular electrodes in body tissue.

FIG. 1 is a diagrammatic view in longitudinal section of a current density distribution obtained as the outcome of a simulation calculation by the inventors, along a bipolar electrode arrangement 10 with a pointed electrode 12 and an annular electrode 13 fixed axially at a spacing relative to the tip electrode 12 by an insulating electrode carrier 11 and insulated with respect to the tip electrode 12 in the body tissue 14. The portion of the electrode arrangement 10 in proximal relationship to the annular electrode 13 is surrounded by an insulating casing 15. Besides the view in longitudinal section, the FIG. also lists in table form the maximum current density (max) and the current density stages a through g which form the basis involved in representing the stimulation result.

It can already be seen at the few current density areas which can be seen at all in the longitudinal section, from the Table (essentially only the areas represented by the lines a through g), that current density peaks occur at the tip and in each of the boundary regions of the electrodes 12, 13 in relation to the insulating portions 11, 15 of the arrangement and the current density overall already falls severely at a small distance from the surfaces. This shows that it is to be assumed that by far the greatest part of the electrical energy which is introduced into the body tissue 14 by the electrode arrangement 10 is converted into thermal energy in the tissue regions immediately adjoining the electrode surfaces. Tissue coagulation begins in the zones of highest current density at the mutually facing electrode edges.

Figure 2:
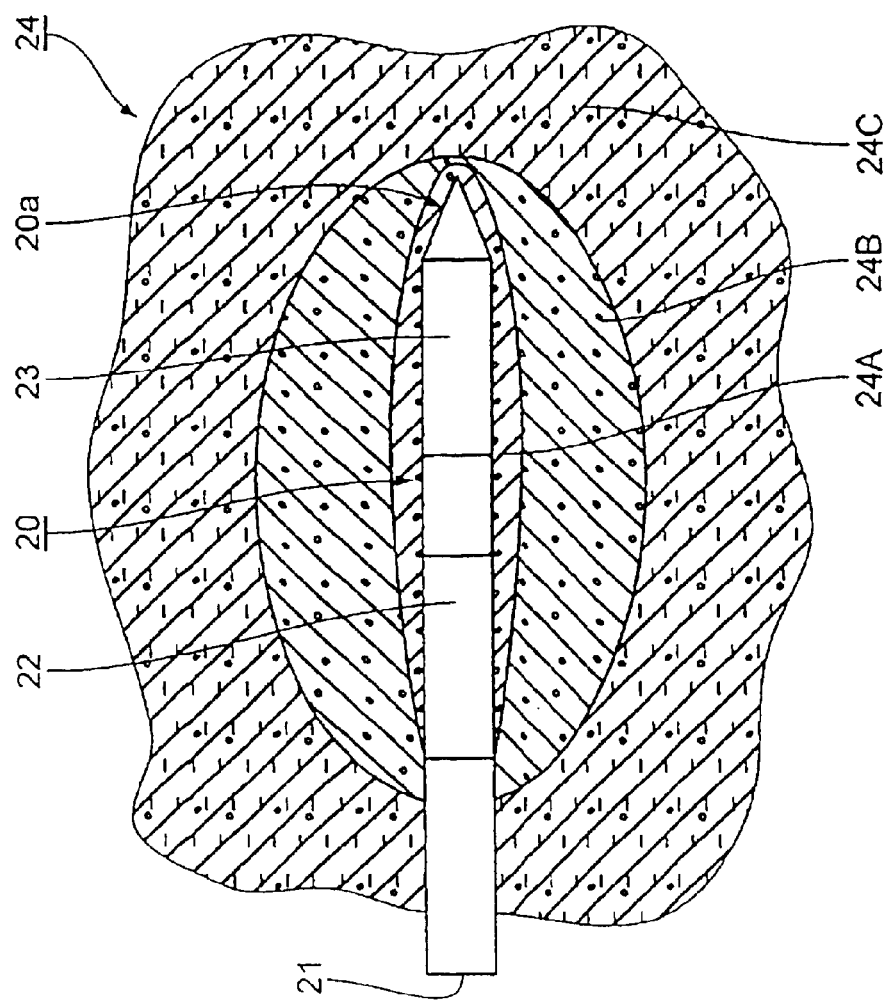
FIG. 2 is a diagrammatic view of the tissue conditions which are formed around an electrode arrangement shown in FIG. 1 without temperature control.

As is diagrammatically shown in FIG. 2, that results in the formation of a drying-out zone approximately in the configuration of a narrow rotational ellipsoid around an electrode arrangement of that kind. The electrode arrangement 20 shown in FIG. 2—in a slightly modified form in comparison with the configuration shown in FIG. 1—includes two cylindrical electrodes 22, 23 of equal length which are fitted into a cylindrical carrier 21, while the tip 20a is here of an insulating nature. The surrounding tissue 24 is divided depending on the temperature and the changes in tissue produced thereby into the drying-out zone 24A, a coagulation zone 24B and a structurally unchanged ("native") outer region 24c. In addition, particularly with a high level of power being introduced, a carbonization layer or zone (not shown in the Figure) can be formed directly at the surface of the arrangement.

The formation of the drying-out zone 24A dramatically worsens the electrical properties of the treatment region, in regard to an electrosurgical treatment. The increase in impedance as a result of the disappearance of tissue fluid results in a considerable reduction in the level of electrical energy which is coupled into that zone and thus overall into the tissue 24. In addition a carbonization zone represents a region of low thermal conductivity and additionally worsens the treatment efficiency.

Figure 5A:
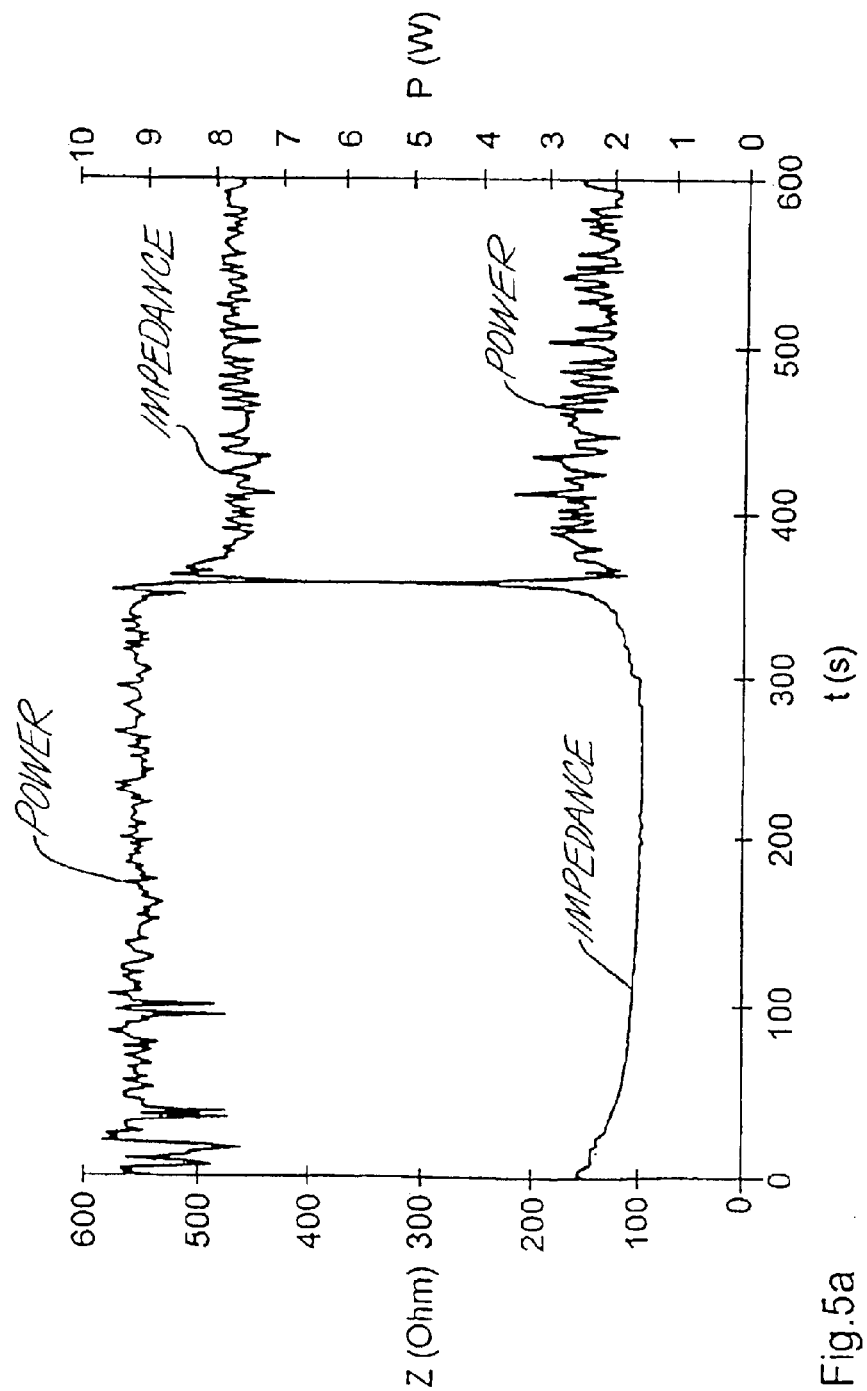
FIGS. 5a and 5b show comparative views of the time-dependency of the tissue impedance measured in the course of a coagulation treatment and the electrical power outputted to the tissue in the case of a non-temperature-controlled and a temperature-controlled electrode arrangement.

That was confirmed by measurements taken by the inventors, as FIG. 5a shows. FIG. 5a is a representation of the time-dependency of the tissue impedance measured in the course of a coagulation treatment, and the electrical power outputted to the tissue, in an electrode arrangement which does not involve temperature control. It can be seen from FIG. 5a that, after an initial fall which is thought to be attributed to the agglomeration or accumulation of tissue fluid at the electrode surface, the impedance is almost constant at a value of around 100Ω over a certain treatment duration. That permits an energy input of about 9 W (in the case of the arrangement which is here set to a maximum power of 10 W). After a treatment duration of about 6 minutes however the impedance suddenly jumps to about four times, as a result of drying-out of the electrode-tissue interface, and that results in a reduction in the electrical power converted to 2–3 W.

Figure 3:
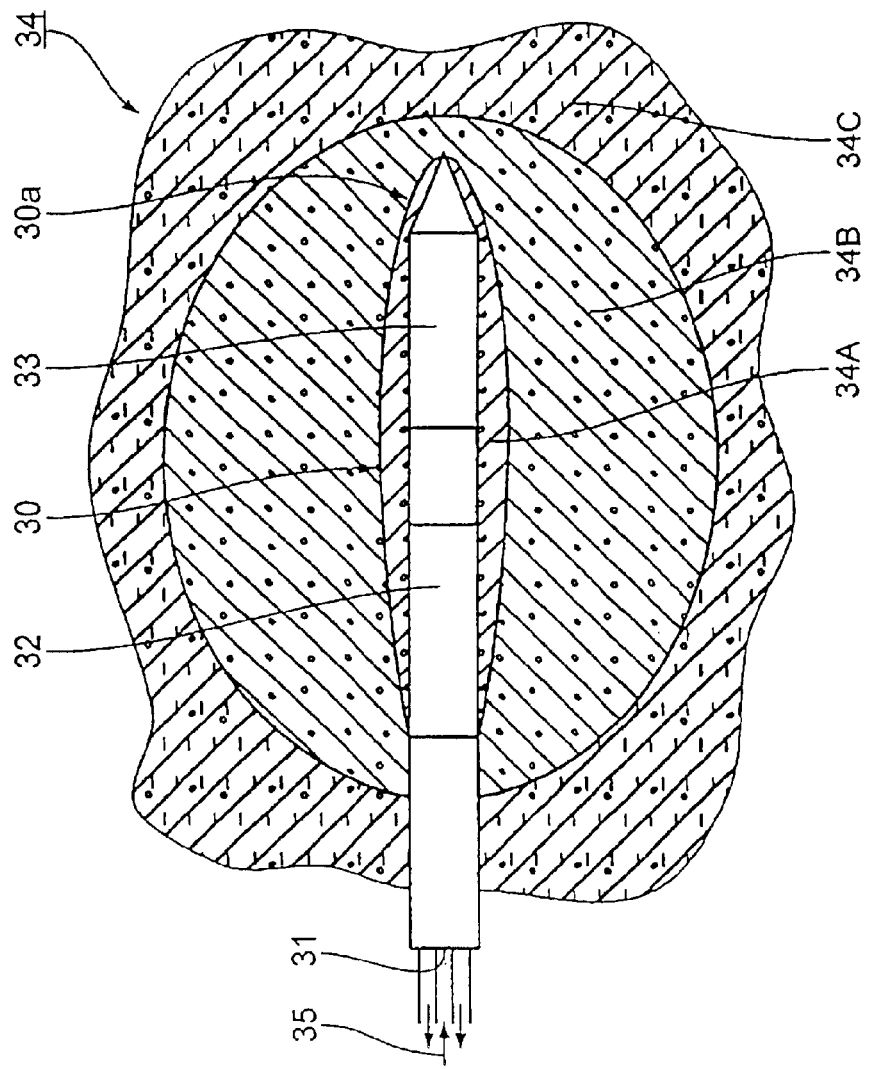
FIG. 3 is a diagrammatic view of the tissue conditions which are formed around an electrode arrangement shown in FIG. 1 with temperature-controlled electrodes.

FIG. 3 diagrammatically shows how the provision of internal temperature control for the electrode arrangement acts on the tissue conditions which are formed in the treatment region. The electrode arrangement 30 diagrammatically shown in FIG. 3 includes—in this respect being in conformity with the structure shown in FIG. 2—two cylindrical electrodes 32, 33 of equal length which are let into a cylindrical carrier 31 and an insulating tip 30a. Reference 35 and the arrows at the proximal end of the illustrated part of the arrangement diagrammatically indicate a fluid counterflow temperature control effect. The surrounding tissue 34 is divided into a relatively cool zone 34A, a coagulation zone 34B and a structurally unchanged outer region 34C. The formation of a carbonization layer is either not observed at all with such an arrangement, or at any event it does not begin directly at the electrode surface.

Figure 4:
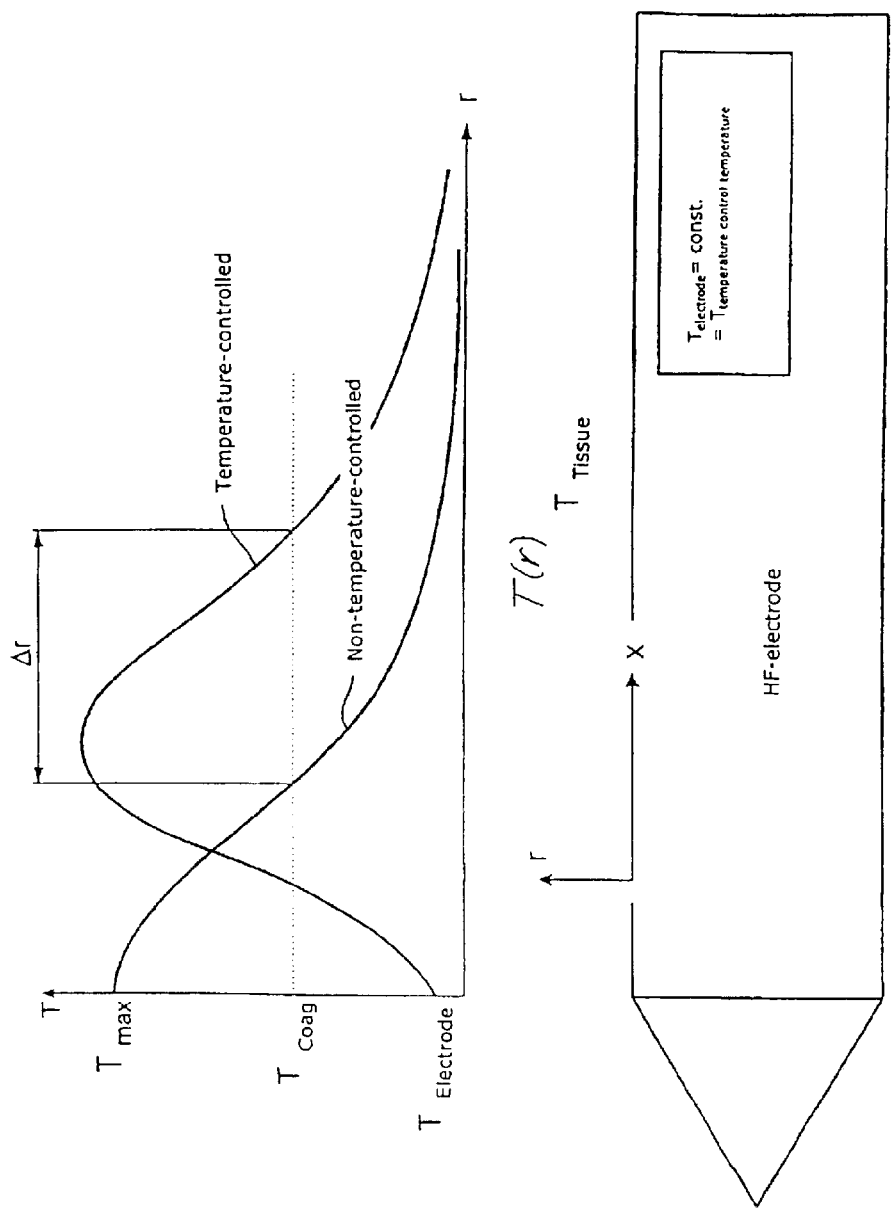
FIG. 4 shows a comparative graph view of the temperature variation in the region of a non-temperature-controlled and a temperature-controlled electrode arrangement in dependence on the spacing from the electrode surface.

The conditions diagrammatically shown in FIG. 3 can also be seen from a comparative graph representation of the spatial variation in temperature in the region of a non-temperature-controlled and a temperature-controlled electrode arrangement, as is shown in the upper region of FIG. 4. The lower part of FIG. 4 represents a sketch to illustrate the values which are linked in the function curves and also the external shape of the electrode arrangement.

It can be clearly seen from the function curves T(r)—which show the conditions at a moment in time shortly after beginning to apply the ac voltage—that the coagulation zone enlarges by a radius difference value Δr, in the case of a temperature-controlled arrangement. That already demonstrates the higher level of efficiency of the cooled arrangement. It is to be noted in regard to the function curve for the temperature-controlled arrangement that—depending on the respective setting of the temperature of the temperature control fluid—in practice the coagulation temperature is also exceeded in the electrode interface region after a certain period of treatment, so that treatment success also occurs in that region.

Figure 5B:
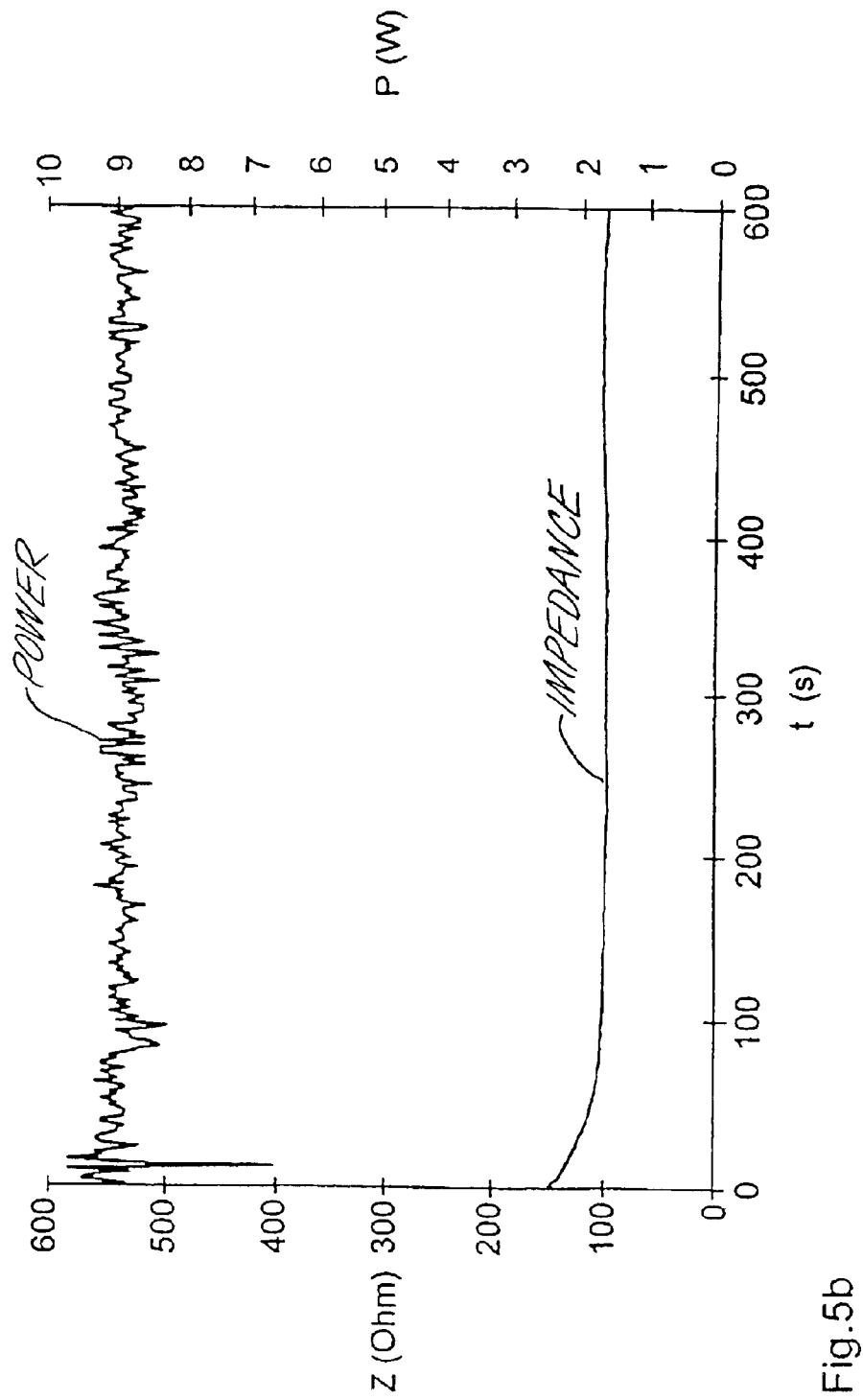

FIG. 5b shows the time-dependency of the tissue impedance and the electrical power outputted to the tissue, when using a temperature-controlled electrode arrangement. It will be seen that the impedance (once again after an initial fall) and the converter power remain practically constant over the treatment period.

Figure 6A:
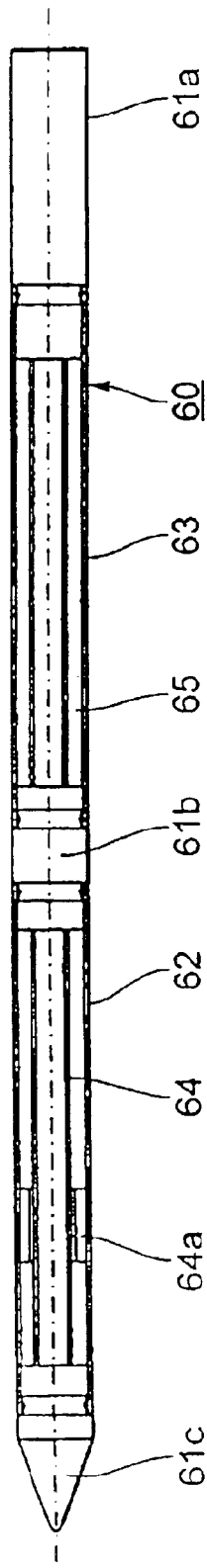
FIGS. 6a and 6b are diagrammatic view in longitudinal section of a bipolar electrode arrangement with two axially mutually displaced fixed annular electrodes and internal fluid temperature control in accordance with an embodiment of the invention.
Figure 6B:
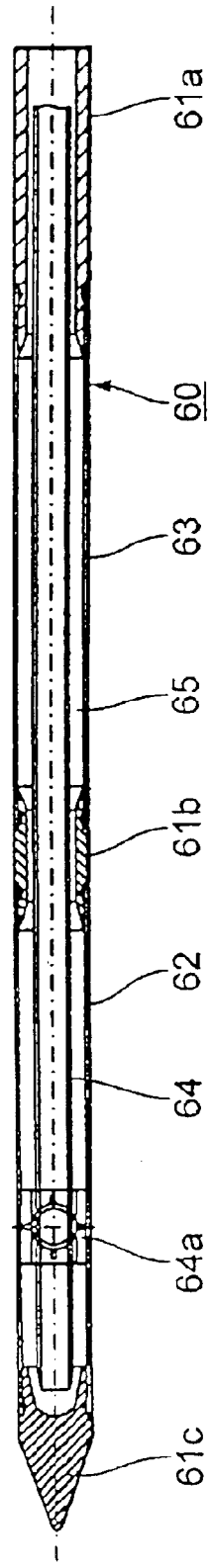

FIGS. 6a and 6b are a partly sectional view and a view in longitudinal section (in different sectional planes) of a temperature-controlled bipolar electrode arrangement 60 as an applicator for HF-induced interstitial thermotherapy of pathological tissue. It includes a tubular plastic carrier 61a, two axially mutually displaced, fixed metal annular electrodes 62, 63 which are fixed and insulated relative to each other by way of an annular plastic intermediate carrier 61b, a plastic tip 61c, an inner tube 64 and an inner tube spacer 64a. The electrodes are connected to an HF-generator by way of lines (not shown in the Figure) comprising highly flexible stranded copper wires.

Depending on the area of use involved, the electrodes 62, 63 are of a diameter in the region of between 1 and 5 mm and are of a length of between 2 and 30 mm. In the illustrated example they are in the form of NITINOL-tubes and are pushed onto the plastic members 61a, 61b and 61c made from high temperature-resistant PEEK (polyethyletherketone) and glued in position thereon by means of high temperature-resistant adhesive. The diameter of the plastic members is adapted to that of the electrodes; the length of the intermediate portion is between 1.5 and 3 times the electrode diameter. The electrode regions which are disposed on the plastic members are coated with PTFE. The inner tube 64 comprises PTFE. Instead of the materials specified, it is also possible to use other tried-and-tested biocompatible materials which are easily slidable into body tissue and which are sufficiently temperature-resistant.

In order to guarantee easy duct-forming insertion directly into body tissue, besides the applicator being of a suitable configuration, the use of polished electrodes and possibly a slip or anti-friction coating are of advantage.

The electrode arrangement 60 is operated with an HF-power of up to 100 W (in the treatment of liver metastases or benign prostate hyperplasia, for example, 50–60 W). The temperature control medium introduced into the inner tube 64 is sterile distilled water at a temperature which is adjustable in dependence on time in the range of between 0 and 80° C. (for example upon introduction and at the beginning of the electrothermy treatment above 30° C. and then ambient temperature) under a pressure of between 0 and 3 bars (for example 1 bar) at a flow rate of up to 200 ml/min (in the above-indicated example 40–60 ml/min). The water flows through the inner tube to the distal end thereof in the region of the tip 61c, it there passes into the annular space 65 between the inner tube and the outer wall of the arrangement and it flows back in the annular space to the exterior of the body where it is drained away.

Figure 7:
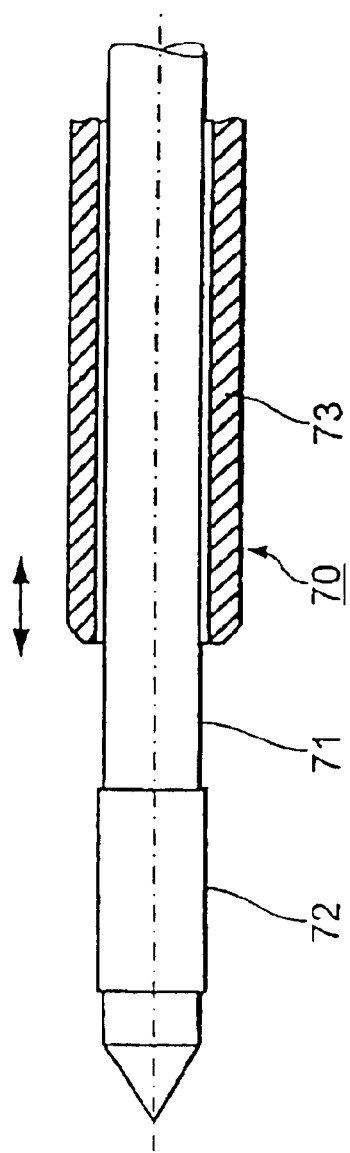
FIG. 7 is a diagrammatic view of a bipolar electrode arrangement with mutually displaceable electrodes and internal temperature control in accordance with a further embodiment of the invention.

Finally, FIG. 7 is a diagrammatic view of a further electrode catheter 70 which permits adjustment of the electrode spacing in order to be able to influence the field and current density distribution in the therapy area. For that purpose the catheter 70 has a cylindrical carrier element 71 of electrically insulating material, in the proximity of the distal end of which is disposed a first electrode 72, in the form of an annular metal coating. In its insulating region the carrier element 71 is axially displaceably guided by a second electrode 73 which extends around it and which is of a hollow-cylindrical configuration, in order to be able to adjust the electrode spacing and thus to make available an additional optional way of varying the effective temperature profile in the treatment region.

Figure 8:
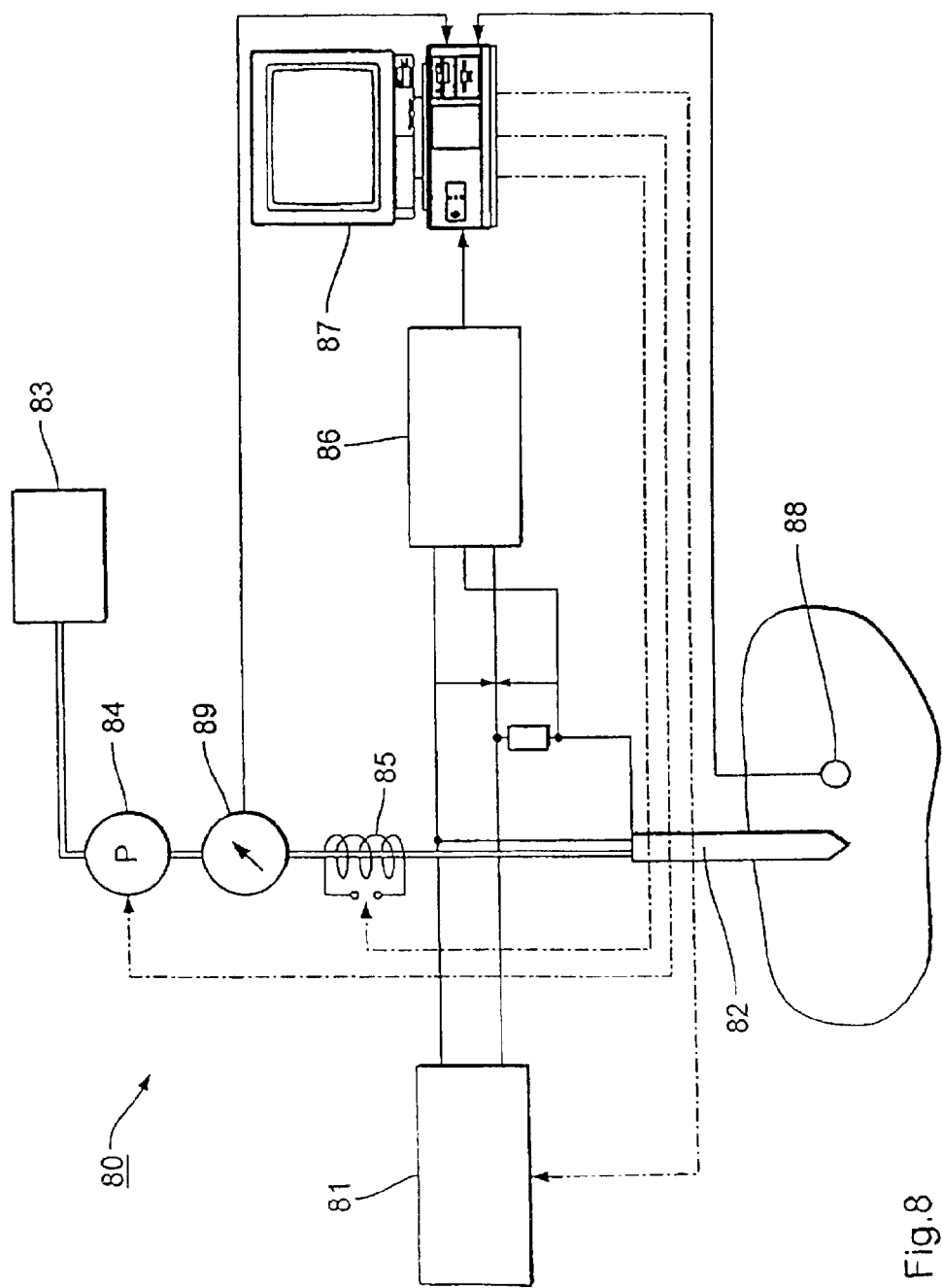
FIG. 8 is a diagrammatic view showing the principle of an electrosurgery apparatus with measuring arrangement for determining essential treatment values.

FIG. 8 is a diagrammatic view showing the principle of an electrosurgery apparatus 80 with an HF-generator 81, an electrode catheter 82 (also referred to as an "HF-needle"), a temperature control fluid container 83, a temperature control fluid pump 84 and a temperature control fluid heater 85, as well as a measuring and evaluation arrangement for establishing essential treatment values. The measuring and evaluation arrangement here includes a storage oscilloscope 86 for detecting the electrical values, a quantitative flow meter 89 for detecting the temperature control fluid flow rate, a T-sensor 88 arranged in the treatment region, and a PC 87 connected by way of a suitable measurement data interface to the measuring devices 86, 88 and 89, for evaluation of the measurement values.

By virtue of the choice of suitable control members, for example a controllable HF-generator 81, a controllable fluid pump 84 and a controllable fluid heater 85 which are connected by control lines (shown in dash-dotted line in FIG. 8) to the PC 87 (or a separate control unit connected to the PC), this arrangement can be used to control the essential treatment values, HF-output power and heating or cooling output, in the course of an electrosurgical intervention, on the basis of active power measurement and impedance measurement and/or temperature measurement in the treatment space.

In particular, for the insertion phase, the fluid temperature and therewith (HF-generator switched off) the temperature of the HF-needle can be raised by means of the fluid heater 85 to a value in the region of body temperature (e.g., about 37° C.) or above. In this phase the fluid pump 84 can be operated with a relatively low delivery or intermittently and a T-regulation action can possibly be omitted. After positioning of the HF-needle and when the HF-generator is switched on—or even better with a time delay after it is switched on, such time delay being predetermined or derived from signals from the T-sensor—the fluid heater is switched off. In that phase, in the normal situation, the fluid pump is controlled on the basis of the predetermined target temperature field or range and with evaluation of the signals from the T-sensor, so that T-regulation then takes place. However differentiated actuation of the fluid pump and the fluid heater can also be implemented throughout the entire interventional procedure on the basis of a predetermined time-dependent target temperature field or range which takes account of the particular requirements of the insertion phase.

Figure 9:
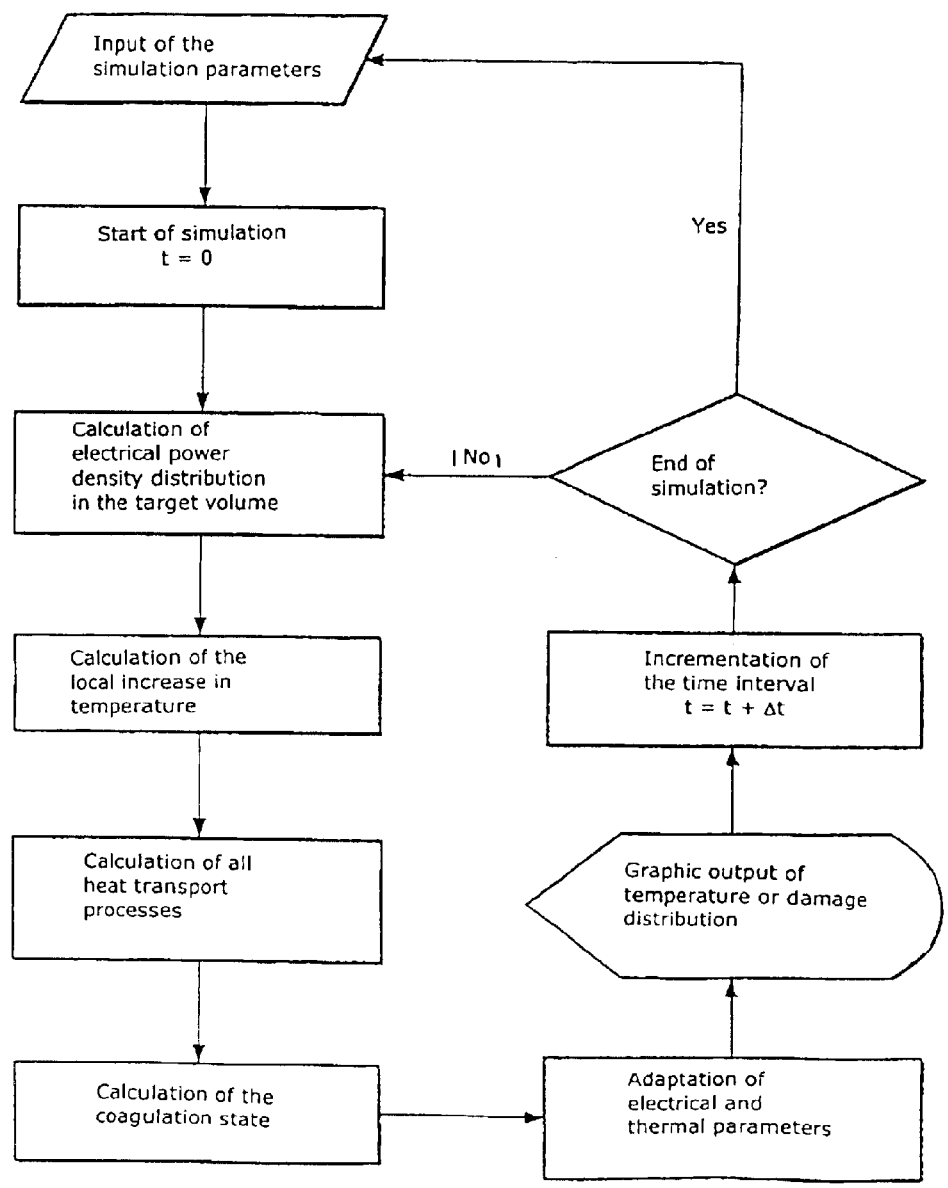
FIG. 9 shows a structure chart of a simulation program for on-line dosimetry in interstitial HF-thermotherapy.

The methodological basis of a representation of therapy progress is a simulation calculation which is based on the method of finite differences to solve the differential equations which describe the electrical and thermal phenomena involved. The fundamental procedure is diagrammatically shown in FIG. 9 which does not require any further commentary.

Figure 10:
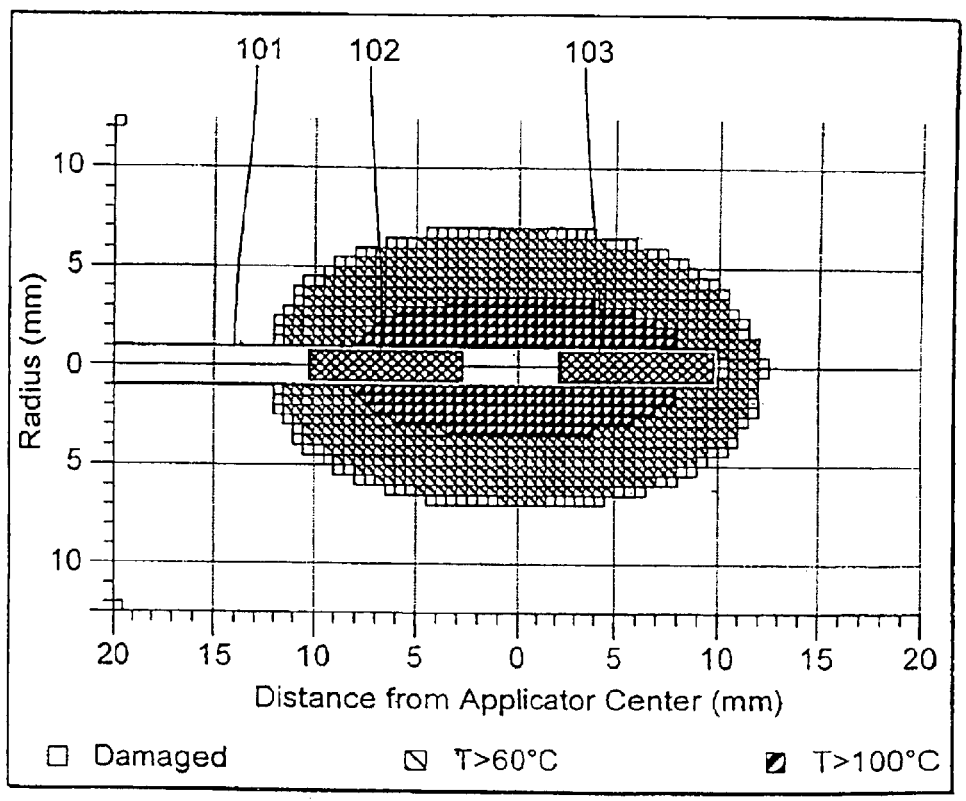
FIG. 10 is a pictorial representation of a simulation event.

FIG. 10 is a pictorial representation of a simulation result as it appears on a computer screen. Illustrated therein are the T-distribution and the limits or boundaries of the treatment region ("Damaged") around an applicator which, on an insulating carrier body 101, carries two electrodes 102 and 103 arranged axially in a row.

Figure 11:
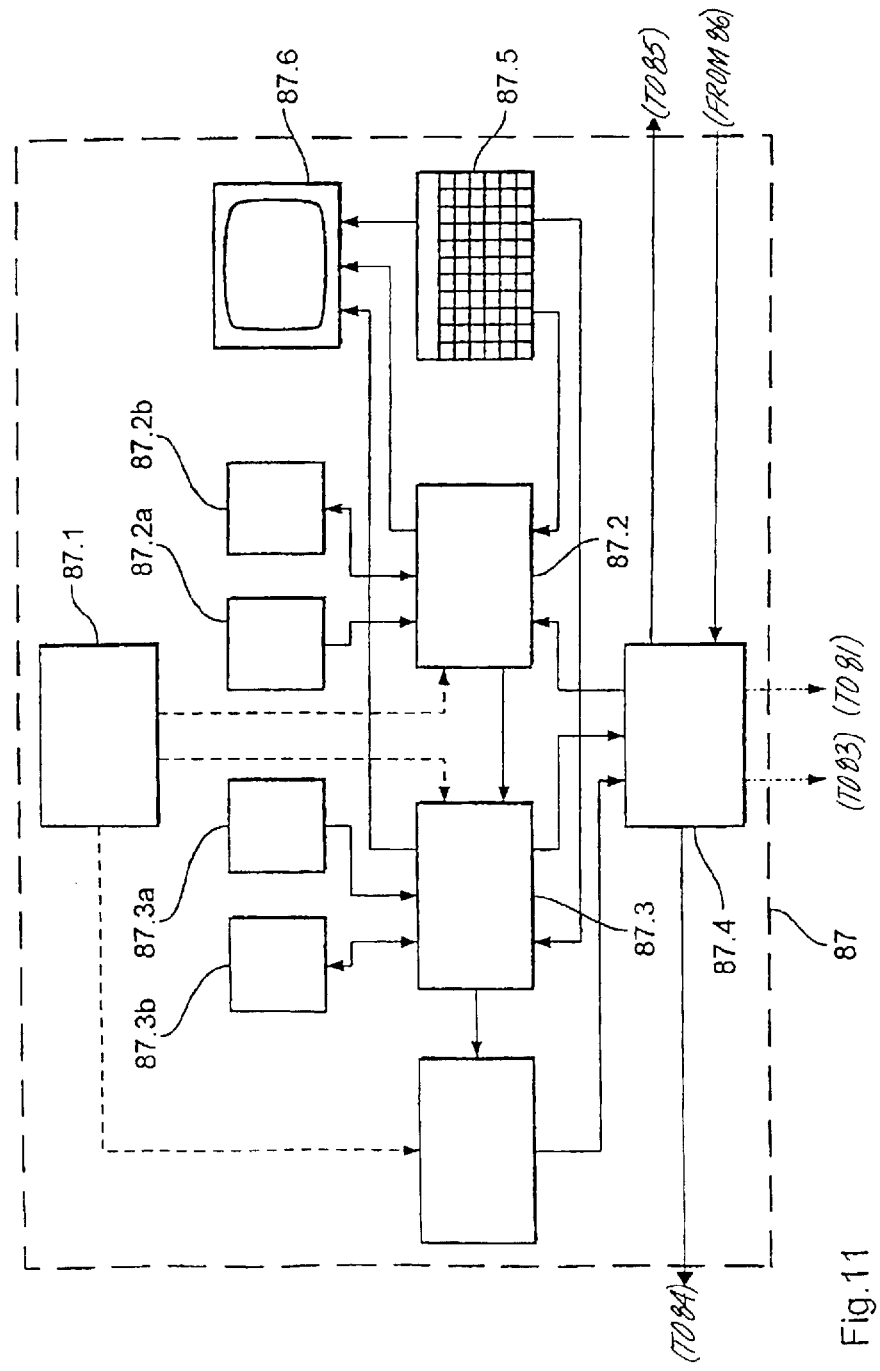
FIG. 11 shows a block circuit diagram of the effective temperature profile control device of the electrosurgery apparatus shown in FIG. 8.

FIG. 11 shows a function block circuit diagram of an embodiment of the integrated evaluation and control device 87 of the HF-applicator system 80 from FIG. 8. The peripheral components are illustrated in FIG. 8 and are therefore omitted from FIG. 11, and also the foregoing description relating to the fundamental control functions is not repeated here in relation to FIG. 11.

The evaluation and control device 87 includes as its main components a procedure control (controller) 87.1, an effective temperature profile calculation unit 87.2 and a control value calculation unit 87.3. Associated with those components in the usual manner are separate program and data stores 87.2a, 87.2b and 87.3a, 87.3b respectively and jointly an I/O-interface 87.4, an input unit 87.5 and a display unit 87.6. The control value calculation unit 87.3 additionally has associated therewith at its output side a control procedure store for storage of calculated time-dependencies of the cooling and heating output control signal whose access control (not shown separately) is connected to the controller 87.1.

The program and the data stores 87.2a, 87.2b of the effective temperature profile calculation unit 87.2 store in particular the above-mentioned simulation program ("dosimetry program") and the data sets which are required for implementation and which can be updated by current inputs by way of the input unit 87.5 on the part of the operator and automatically upon the input of new measurement data, by way of the interface 87.4. Accordingly, in each phase of a treatment—including the duct-forming insertion of the HF-needle—it is possible to acquire a current stimulation result for the effective temperature profile (see FIG. 10) and thus a prognosis about further progress in the treatment.

The program and the data stores 87.3a, 87.3b of the control value calculation unit 87.3 store in particular algorithms and parameter sets which permit an association of specific control data sets with effective temperature profile data sets, possibly also control data tables which are already directly accessible. Complete control data sets for an overall treatment can be advanced into the control procedure store 87.6 after the conclusion of a preparatory or updated simulation calculation, from where they can be outputted by way of the controller 87.1 to the automatic timing control in respect of the treatment parameters for adjustment of the fluid pump 84, the fluid heater 85 and the HF-generator 81 (FIG. 8). In this respect also a corrective intervention on the part of the operator is possible in any phase.

The invention is not limited in terms of its implementation to the preferred embodiments set forth hereinbefore. On the contrary it is possible to envisage a number of alternative configurations which also make use of the claimed solution, in configurations of different kinds.

What is claimed is:

1. An electrosurgery apparatus comprising:
    an electrode carrier having a pointed configuration at a distal end;
    at least one electrode on the electrode carrier;
    a fluid flow path defined in the electrode carrier;
    an alternating current source conductively connected to the electrode by way of a cable providing alternating current flow to said at least one electrode;
    a temperature control device for the electrode and the electrode carrier; and
    a fluid heater for heating the at least one electrode and the electrode carrier independent of the amplitude of the alternating current flowing through the at least one electrode.

2. An electrosurgery apparatus as set forth in claim 1 wherein the at least one electrode and the electrode carrier are heatable to a temperature of more than 30° C.

3. An electrosurgery apparatus as set forth in claim 2 wherein the at least one electrode and the electrode carrier are heatable to a temperature of more than 37° C.

4. An electrosurgery apparatus as set forth in claim 3 comprising:
    a cavity in one of the at least one electrode and the electrode carrier; and
    wherein the temperature control device includes a temperature-controllable fluid source which is in communication with one of the at least one electrode and the electrode carrier by way of a quantitative flow control device.

5. An electrosurgery apparatus as set forth in claim 1 wherein a fluid source provides a fluid to the fluid flow path.

6. An electrosurgery apparatus as set forth in claim 1 comprising an effective temperature profile control device which is coupled to the temperature control device.

7. An electrosurgery apparatus as set forth in claim 6, wherein the effective temperature profile control device is coupled to the alternating current source, for sending a control input for controlling the alternating current source.

8. An electrosurgery apparatus as set forth in claim 1 comprising two electrodes.

9. An electrosurgery apparatus as set forth in claim 1 wherein fluid flows through the flow path toward the distal end of the apparatus and back in a direction away from the distal end.

10. An electrosurgery apparatus as set forth in claim 1 wherein the at least one electrode is annular and wherein the flow path is defined within said at least one electrode.

11. An electrosurgery apparatus as forth in claim 1 further comprising a tube within the electrode wherein the flow path is defined through the tube.

12. An electrosurgery apparatus as set forth in claim 11 wherein an annulus is defined between the tube and the at least one electrode and wherein the fluid flow path is defined in a distal direction within the tube and in a direction away from the distal end within the annulus.

13. An electrosurgery apparatus as set forth in claim 1 further comprising a fluid flowing through the flow path for controlling the temperature of the apparatus.

14. An electorsugery apparatus as set forth in claim 13 wherein the fluid is heated by the fluid heater for heating the at least one electrode and the electrode carrier independent of the amplitude of the alternating current flowing through the at least one electrode.

15. An electrosurgery apparatus as set forth in claim 13 wherein the fluid is distilled water.

16. A method for electrothermal treatment of a human or animal patient comprising:
    providing an electrosurgery apparatus comprising,
    an electrode carrier having a pointed configuration at its distal end,
    at least one electrode on the electrode carrier, and
    a fluid flow path defined in the electrode carrier;
    preheating the apparatus prior to an electrothermal treatment of a tissue in an area to be treated;
    inserting the apparatus in the area of the patient to be treated such that the distal end is adjacent to the tissue in the area to be treated;
    providing alternating current to the electrode for electrothemally treating the tissue; and
    providing a fluid within the fluid flow path for controlling the temperature of the apparatus.

17. The method as recited in claim 16 wherein varying the temperature of the fluid varies the temperature of the apparatus.

18. The method as set forth in claim 16 wherein inserting further comprises controlling the temperature of the fluid for controlling the temperature of the apparatus to be above about 30° C.

19. The method as set forth in claim 18 further comprising varying the temperature of the fluid when the distal end is adjacent to the tissue for varying the temperature of the apparatus.

20. The method as recited in claim 16 further comprising providing a tube within the apparatus for defining the flow path.

21. The method as recited in claim 20 further comprising defining an annulus between the tube and the at least one electorde and flowing the fluid through the tube distally toward the distal end and back away from the distal end through the annulus.

22. A method for electrothermal treatment of a human or animal patient comprising:

providing an electrosurgery apparatus comprising, an electrode carrier having a pointed configuration at its distal end, at least one electrode on the electrode carrier, and a distilled water flow path defined in the electrode carrier;

inserting the apparatus in an area of the patient to be treated such that the distal end is adjacent to a tissue in the area to be treated;

providing alternating current to the electrode for electrothemally treating the tissue; and providing distilled water within the distilled water flow path for controlling the temperature of the apparatus.

23. The method as recited in claim 22 wherein varying the temperature of the distilled water varies the temperature of the apparatus.

24. The method as set forth in claim 22 wherein inserting further comprises controlling the temperature of the distilled water for controlling the temperature of the apparatus to be above about 30° C.

25. The method as set forth in claim 24 further comprising varying the temperature of the distilled water when the distal end is adjacent to the tissue for varying the temperature of the apparatus.

26. The method as recited in claim 22 further comprising providing a tube within the apparatus for defining the flow path.

27. The method as recited in claim 26 further comprising defining an annulus between the tube and the at least one electorde and flowing the distilled water through the tube distally toward the distal end and back away from the distal end through the annulus.

* * * * *